Figure 1:
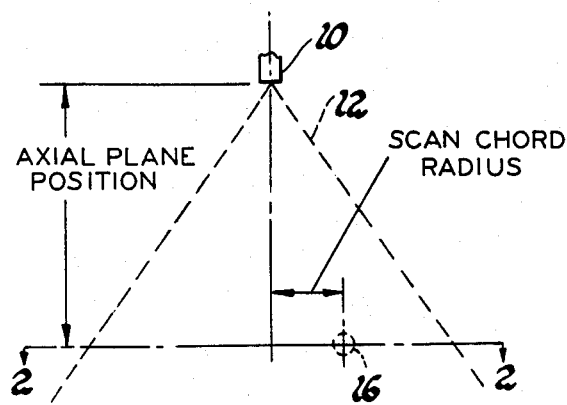

United States Patent [19]

Chraplyvy et al.

[11] Patent Number: 4,470,697

[45] Date of Patent: Sep. 11, 1984

[54] METHOD OF MEASURING THE CONCENTRATION OF GAS IN THE PRESENCE OF LIQUID PARTICLES

[75] Inventors: Andrew R. Chraplyvy, Matawan, N.J.; Dean C. Hammond, Jr., Birmingham; Julian M. Tishkoff, Troy, both of Mich.

[73] Assignee: General Motors Corporation, Detroit, Mich.

[21] Appl. No.: 262,190

[22] Filed: May 11, 1981

[51] Int. Cl.$^3$ ............................................. G01N 21/00
[52] U.S. Cl. .......................................... 356/73; 73/23; 250/573
[58] Field of Search ............... 250/338, 340, 341, 343, 250/345, 573; 356/73, 335, 336, 338, 407, 409, 435, 437, 438, 439; 73/23; 162/49, 198, 238

[56] References Cited

U.S. PATENT DOCUMENTS

| | | | |
|---|---|---|---|
| 3,817,622 | 6/1974 | Billman et al. | 356/73 |
| 3,843,258 | 10/1974 | Shupe | 250/573 X |
| 3,895,233 | 7/1975 | Boll et al. | 356/435 X |
| 4,001,595 | 1/1977 | Reismann | 250/573 X |
| 4,154,089 | 5/1979 | Carlon | 250/343 X |
| 4,394,575 | 7/1983 | Nelson | 250/343 |

OTHER PUBLICATIONS

Swithenbank et al.,–"Progress in Astronautics and Aeronautics", vol. 53, pp. 421-447, 1977.

Primary Examiner—Vincent P. McGraw
Attorney, Agent, or Firm—Warren D. Hill

[57] ABSTRACT

To evaluate the droplet evaporation and liquid/vapor phase interactions in aerosols and sprays, an optical method for measuring the concentration of the gas phase is provided. Two laser beams are passed through a mixture of the gas and liquid particles, one beam having a wavelength not absorbed by the gas and the second having a wavelength which is absorbed by the gas. Attenuation of each beam is measured, the droplet size distribution is measured by a light scattering technique and the concentration of gas in the path of the light beams is determined from the attenuation of each beam, the droplet size distributions, and known parameters.

3 Claims, 3 Drawing Figures

U.S. Patent   Sep. 11, 1984   4,470,697

METHOD OF MEASURING THE CONCENTRATION OF GAS IN THE PRESENCE OF LIQUID PARTICLES

This invention relates to a method of measuring the concentration of gas in the presence of liquid particles and particularly to such a method using non-intrusive optical means.

In order to understand the droplet evaporation and the liquid/vapor phase interactions in aerosols and sprays, it is desirable to measure the liquid and vapor phases separately to determine the concentration of the vapor as well as the size distribution and number density of the liquid particles. Such studies are useful, for example, in studies of fuel spray vaporization and combustion. The liquid phase behavior of sprays has been studied with photographic, pulsed laser shadowgraphic and optical scattering techniques. Heretofore, a direct measurement of the vapor phase content in a spray has not been accomplished by non-intrusive methods. Any physical probe inserted into a spray to capture vapor samples for subsequent analysis disrupts the air and droplet flows and subsequently does not reflect the true vapor distribution in the spray. Optical techniques are not intrusive but in the past have been severely hampered by droplet scattering and absorption of the probe radiation.

It is therfore an object of the invention to provide a non-intrusive method for the measurement of gas or vapor concentration in a mixture of gas and liquid particles.

The invention is carried out by passing two monochromatic beams of radiation along the same path through the mixture of gas and liquid particles, one beam having a wavelength not absorbed by the gas and the other having a wavelength which is absorbed by the gas, measuring the attenuation of each beam, determining the droplet size distribution in the mixture of gas and liquid particles, and determining from the attenuation of each beam and the droplet size distribution the concentration of gas in the path of the light beams.

Figure 2:
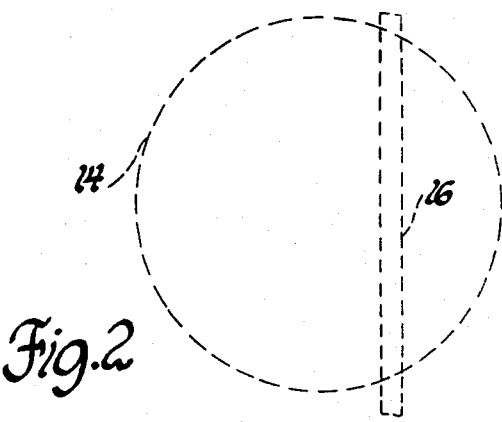
Figure 3:
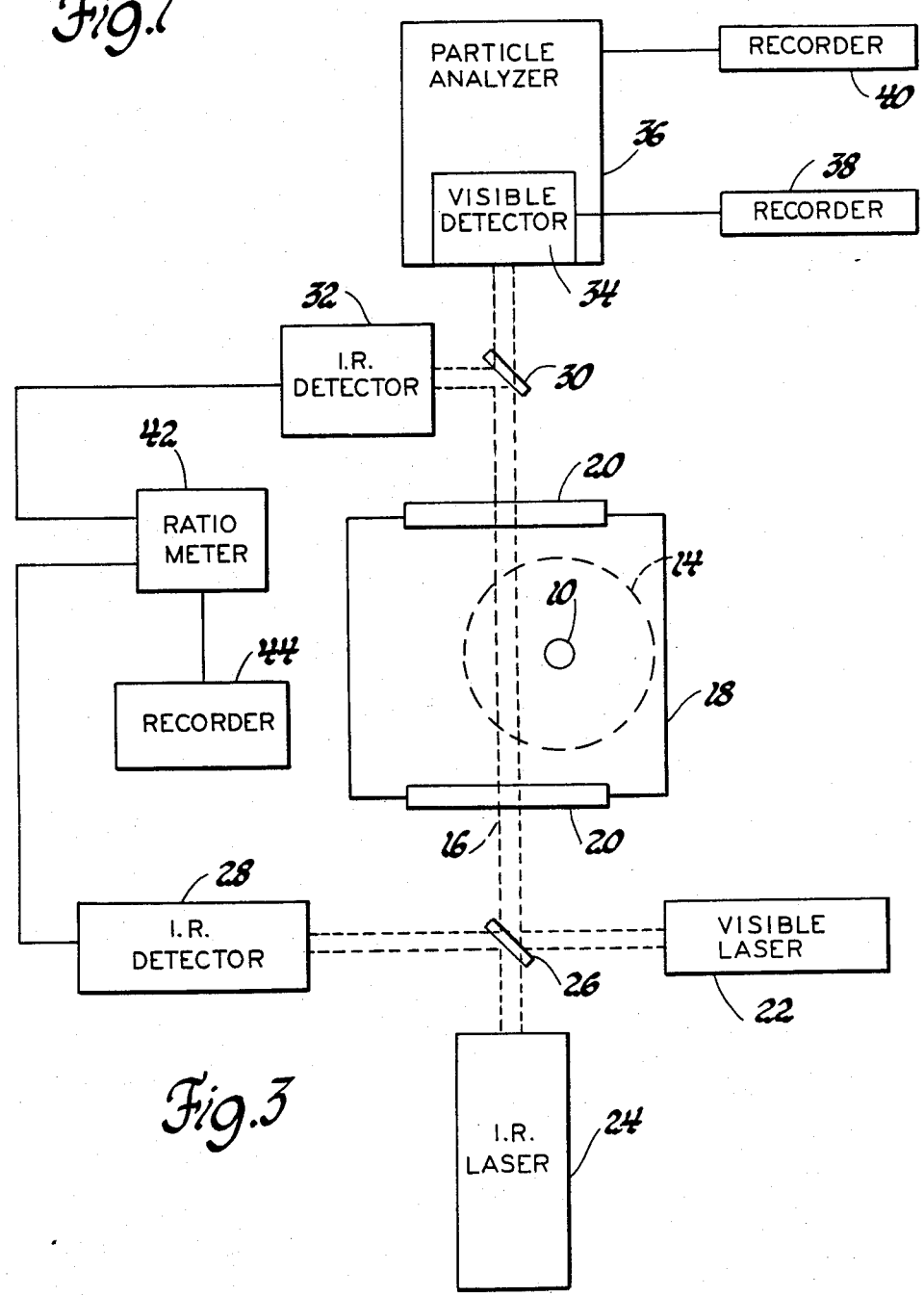

The above and other advantages will be made more apparent from the following specification taken in conjunction with the accompanying drawings wherein like reference numerals refer to like parts and wherein:

FIGS. 1 and 2 are top and front views respectively of a spray pattern emitted from a nozzle and a light beam probe passing therethrough, and FIG. 3 is a schematic view of apparatus suitable for making measurements useful to carry out the method according to the invention.

Although the method of the invention is of general utility for measuring gas or vapor concentrations in the presence of liquid particles, it is described herein in terms of a fuel spray analysis technique. This technique is also described in the article of Tishkoff, J. M., Hammond, Jr. D. C., and Chraplyvy, A. R., "Diagnostic Measurements of Fuel Spray Dispersion" ASME publication 80-WA/HT-35 (1980) which is specifically incorporated herein by reference.

FIG. 1 shows a fuel nozzle 10 such as a simplex pressure atomizing nozzle emitting a spray of fuel in a generally conical pattern bounded by the dotted lines 12. The cross section 2—2 of the spray pattern has a circular boundary 14 as shown in FIG. 2. A light path through the spray pattern is shown as a cylindrical beam 16. The path will be placed in various locations in the spray pattern for the measurement of the vapor concentration in each location. As shown in FIG. 3, the nozzle 10 and spray pattern are contained within a spray tunnel 18 having windows 20. The beam 16 originates from two lasers 22 and 24 which have individual beams combined by a beam splitter 26 to follow the same path through the spray. The lasers operate either simultaneously or separately. The lasers operate at different wavelengths chosen so that one wavelength will not be absorbed by the vapor being measured but the other wavelength will be absorbed. As a specific example, where the fuel spray being tested comprised heptane the laser 22 was selected to provide a visible light beam at 0.6328 $\mu$m and the laser 24 was selected to emit an infrared beam having a wavelength of 3.39 $\mu$m. Both wavelengths are smaller than the liquid particles in the spray. The beam splitter 26 is selected to have a reflective coating which reflects substantially all of the visible light along the path 16 through the spray pattern and reflects a portion of the infrared light to an infrared reference detector 28 and passes the remainder along the path 16 through the spray pattern.

A beam emerging from the spray pattern is directed to a second beam splitter 30 which is reflectively coated in a way to reflect the infrared beam to an infrared detector 32 and to pass the visible light to a visible light detector 34 which is an integral part of a particle analyzer 36. The detector 34 has its output connected to a chart recorder or other recording device 38. The particle analyzer 36 has its output connected to a chart recorder or other recording device 40.

The particle analyzer senses forward scattered visible light from the spray pattern and by analysis of the scattered light pattern determines the particle size distribution in the path of the beam 16. This particle analyzer is fully described in the article:

Swithenbank, J. Beer, J. M. Taylor, D. S., Abbot, D., and McCreath, G. C., "A Laser Diagnostic Technique for the Measurement of Droplet and Particle Size Distribution," Progress in Astronautics and Aeronautics, Vol. 53, Experimental Diagnostics in Gas Phase Combustion Systems, Edited by B. T. Zinn, New York: American Institute of Aeronautics and Astronautics, 1977.

Further the analyzer is commercially available as particle sizer model or model 2200 manufactured by Malvern Instruments, Malvern, England. Thus for a given test, the recorder 40 makes a record of the particle size distribution in the spray pattern.

The output of the infrared detector 32 and the output of the infrared detector 28 are each connected to a ratio meter 42, the output of which is connected to a chart recorder or other recording device 44. When the outputs of the detectors 28 and 32 are normalized by adjusting them to provide equal outputs when there is no spray absorption, the ratio meter will calculate the attenuation of the infrared beam by the liquid/vapor mixture. Similarly, when the visible light detector 34 is normalized to provide a unity reading in the absence of a spray, the output of the detector will represent the attenuation of the visible light by the spray during a test.

The attenuation of either beam is given by $$\frac{I(\lambda)}{I_0(\lambda)} = e^{-C\alpha(\lambda)L}e^{-\eta E(\lambda)L} \quad \text{(Equation 1)}$$

where $I(\lambda)$ = transmitted intensity through the sample volume $I_o(\lambda)$ = intensity entering the sample volume = laser wavelength C = vapor concentration L = length of sample volume $\alpha(\lambda)$ = absorption coefficient of vapor $\eta$ = droplet number density $E(\lambda)$ = average extinction cross-section of droplets The average extinction cross-section $E(\lambda)$ can be calculated on the basis of Mie theory and the measured droplet size distribution as registered in recorder 40 as $$E(\lambda) = \frac{\pi}{4} \int_0^\infty Q(\lambda) \frac{dn}{dD} D^2 \, dD \qquad \text{(Equation 2)}$$

where $Q(\lambda)$ = extinction efficiency $dn/dD$ = droplet-size distribution

D = droplet diameter

The extinction efficiency $Q(\lambda)$ is a value known in the art for each wavelength and the complex refractive index of the droplets and is calculable from data available in the literature. The droplet size distribution $dn/dD$ is the particle size measurement performed by the analyzer 36 and stored in the recorder 40. Thus, the value $E(\lambda)$ is readily obtained for each wavelength. In the case of the first wavelength, $\lambda_1 = 0.6328$ μm and the absorption coefficient $\alpha = 0$ since the first wavelength is selected to have no absorption by the vapor being measured. Thus, the general equation for the attenuation of the visible beam which was measured by the detector 34 and stored in recorder 38 reduces to $$\frac{I(\lambda_1)}{I_o(\lambda_1)} = e^{-\eta E(\lambda_1)L}$$

which can be restated as $$\eta = -\ln \frac{I(\lambda_1)}{I_o(\lambda_1)} \left( \frac{1}{E(\lambda_1)L} \right).$$

Since L is directly measurable as the length of the light beam in the spray pattern, the value of the droplet number density $\eta$ is directly calculated.

The equation 1 can be rewritten as follows to obtain an expression for the vapor concentration $$C: C = -\frac{1}{\alpha L} \left[ \ln \frac{I(\lambda_2)}{I_o(\lambda_2)} + \eta E(\lambda_2) L \right].$$

The attenuation of the infrared light, $I(\lambda_2)/I_o(\lambda_2)$, is the value stored in the recorder 44. The value $\eta$ was previously determined and the value of the average extinction cross-section for the infrared wavelength $E(\lambda_2)$ is determined by equation 2. The absorption coefficient $\alpha$ for the infrared wavelength is found in the literature. Thus, all the terms are known and the vapor concentration C is readily determined.

It will thus be seen that the method of this invention permits the measurement of vapor concentration in the midst of liquid droplets by passing two beams of monochromatic light through the sample, one of the beams having a wavelength not absorbed by the vapor and the other having a wavelength which is absorbed by the vapor. The particle size distribution is measured by standard instrumentation and the attenuation of each wavelength is measured by a simple optical arrangement. These measured values along with known absorption coefficient of a given vapor at a given wavelength and the extinction efficiency of droplets of various diameters which is also known allows the determination of the vapor concentration C from the formulae given herein. The end result is that for the first time the vapor concentration is a mixture of vapor and liquid particles can be measured without physical intrusion.

The embodiments of the invention in which an exclusive property or privilege is claimed are defined as follows:

1. A method of measuring the concentration of gas in the presence of liquid particles comprising the steps of
passing first and second monochromatic collimated beams along the same path through a mixture of the gas and liquid droplets, the first beam having a wavelength which is not absorbed by the gas and the second beam having a wavelength which is absorbed by the gas, and both wavelengths being smaller than the liquid droplets,
measuring the attenuation of each beam,
determining the droplet size distribution in the beam, and
determining the concentration of gas in the beam path from the attenuation of each beam and the droplet size distributions.

2. A method of measuring the concentration of gas in the presence of liquid particles comprising the steps of
passing first and second laser beams along the same path through a mixture of the gas and liquid droplets, the first beam having a wavelength which is not absorbed by the gas and the second beam having a wavelength which is absorbed by the gas, and both wavelengths being smaller than the liquid droplets,
measuring the attenuation of each beam,
measuring forward scattered light distributions,
calculating the droplet size distribution from the forward scattered light distributions, and
determining the concentration of gas in the beam path from the attenuation of each beam, the droplet size distributions, and known parameters.

3. A method of measuring the concentration of gas in the presence of liquid particles comprising the steps of
passing first and second laser beams along the same path through a mixture of the gas and liquid droplets, the first beam having a first wavelength which is not absorbed by the gas and the second beam having a second wavelength which is absorbed by the gas, and both wavelengths being smaller than the liquid droplets,
measuring the attenuation of each beam,
measuring the beam path length through the mixture,
measuring forward scattered light distributions,
calculating the droplet size distribution from the forward scattered light distributions,
determining for each wavelength the average extinction cross-section of the liquid droplets on the basis of the said droplet size distribution and known values of extinction efficiency,
determining the droplet number density from the measured attenuation of the first beam, the average extinction cross-section of the liquid droplets for the first wavelength and the measured length of the beam path, and determining the concentration of gas in the beam path from the known value of the gas absorption coefficient at the second wavelength, the length of the beam path, the attenuation of the second beam, the average extinction cross-section of the droplets for the second wavelength and the droplet number density.

* * * * *

UNITED STATES PATENT AND TRADEMARK OFFICE
CERTIFICATE OF CORRECTION

PATENT NO. : 4,470,697
DATED : September 11, 1984
INVENTOR(S) : Andrew R. Chraplyvy, Dean C. Hammond, Jr., Julian M. Tishkoff It is certified that error appears in the above—identified patent and that said Letters Patent is hereby corrected as shown below:

Column 3, lines 3 and 4;

"$I_o(\lambda)$ = intensity entering the sample volume = laser wavelength"

should read

-- $I_o(\lambda)$ = intensity entering the sample volume $\lambda$ = laser wavelength --.

Column 3, line 15;

"$E(\lambda) = \frac{\Pi}{4} \int_0^\infty Q(\lambda) \frac{dn}{dD} D^2 \, dD$ (Equation 2)"

should read

-- $E(\lambda) = \frac{\Pi}{4} \int_0^\infty Q(\lambda) \frac{dn}{dD} D^2 \, dD$ (Equation 2) --.

Signed and Sealed this

Thirtieth Day of April 1985

[SEAL]

Attest:

DONALD J. QUIGG

Attesting Officer

Acting Commissioner of Patents and Trademarks